US010376156B2

(12) United States Patent
Strauss et al.

(10) Patent No.: US 10,376,156 B2
(45) Date of Patent: Aug. 13, 2019

(54) DEVICE FOR MONITORING FOR EFFECTIVENESS OF HEART FAILURE THERAPY

(71) Applicant: CARDIMETRIX LLC, Teaneck, NJ (US)

(72) Inventors: Benjamin Strauss, Teaneck, NJ (US); Eric Forkosh, Woodmere, NY (US); Kalman Katlowitz, New York, NY (US)

(73) Assignee: CardiMetrix LLC

( * ) Notice: Subject to any disclaimer, the term of this patent is extended or adjusted under 35 U.S.C. 154(b) by 405 days.

(21) Appl. No.: 14/802,094

(22) Filed: Jul. 17, 2015

(65) Prior Publication Data

US 2016/0015276 A1    Jan. 21, 2016

Related U.S. Application Data

(60) Provisional application No. 62/025,683, filed on Jul. 17, 2014.

(51) Int. Cl.
| | | |
|---|---|---|
| *A61B 5/00* | (2006.01) | |
| *A61B 5/08* | (2006.01) | |
| *A61B 5/024* | (2006.01) | |
| *A61B 5/085* | (2006.01) | |
| *G01G 19/50* | (2006.01) | |
| *A61B 5/0205* | (2006.01) | |
| *A61B 5/0245* | (2006.01) | |

(Continued)

(52) U.S. Cl.
CPC .......... *A61B 5/0205* (2013.01); *A61B 5/0006* (2013.01); *A61B 5/0537* (2013.01); *A61B 5/6887* (2013.01); *A61B 5/742* (2013.01); *G01G 19/50* (2013.01); *A61B 5/024* (2013.01); *A61B 5/0245* (2013.01); *A61B 5/02125* (2013.01); *A61B 5/0402* (2013.01); *A61B 5/0535* (2013.01); *A61B 5/085* (2013.01); *A61B 5/0816* (2013.01); *A61B 5/14551* (2013.01);

(Continued)

(58) Field of Classification Search
CPC .... G01G 19/50; A61B 5/0205; A61B 5/0006; A61B 5/0537; A61B 5/742; A61B 5/6887; A61B 5/4023; A61B 5/0245; A61B 5/085; A61B 5/14551; A61B 5/6826; A61B 5/7275; A61B 5/4878; A61B 5/4875; A61B 5/0816; A61B 5/024; A61B 5/14552
USPC ...................................... 600/301; 177/45–50
See application file for complete search history.

(56) References Cited

U.S. PATENT DOCUMENTS 3,508,540 A * 4/1970 Cavallari, Jr. ....... A61B 5/0531
                                                        600/547
5,123,494 A * 6/1992 Schneider ............... A47F 10/02
                                                        177/200

(Continued)

FOREIGN PATENT DOCUMENTS

KR         20060028230 A  *  3/2006

OTHER PUBLICATIONS

Notification of Transmittal of the International Search Report and the Written Opinion of the International Searching Authority, or the Declaration dated Dec. 15, 2015 for International Application No. PCT/US2015/040850.

*Primary Examiner* — Nathan J Jenness
(74) *Attorney, Agent, or Firm* — Barnes & Thornburg LLP

(57) ABSTRACT

A step-on device records the patient's EKG, Respiratory signal, PPG, and weight, giving health care personnel the ability to monitor patient health trends. The device sends the data to a central server via a smartphone or via WiFi. Health care personnel may view the data and trends on an online website or app.

24 Claims, 5 Drawing Sheets

(51) Int. Cl.
  *A61B 5/0402*  (2006.01)
  *A61B 5/1455*  (2006.01)
  *A61B 5/053*   (2006.01)
  *A61B 5/021*   (2006.01)

(52) U.S. Cl.
  CPC ......... *A61B 5/14552* (2013.01); *A61B 5/4023* (2013.01); *A61B 5/4878* (2013.01); *A61B 5/6826* (2013.01); *A61B 5/6829* (2013.01); *A61B 5/7275* (2013.01)

(56) References Cited

U.S. PATENT DOCUMENTS

| | | | |
|---|---|---|---|
| 6,038,465 A | 3/2000 | Melton | |
| 6,402,691 B1 | 6/2002 | Paddicord | |
| 8,475,367 B1 | 7/2013 | Yuen et al. | |
| 2005/0014608 A1 | 1/2005 | Chen | |
| 2007/0021979 A1* | 1/2007 | Cosentino | A61B 5/0031 705/2 |
| 2007/0270707 A1 | 11/2007 | Belalcazar | |
| 2009/0088661 A1* | 4/2009 | Suzuki | A61B 5/0537 600/547 |
| 2010/0076321 A1 | 3/2010 | Zhang et al. | |
| 2010/0094147 A1 | 4/2010 | Inan et al. | |
| 2011/0077536 A1* | 3/2011 | Kubo | A61B 5/022 600/499 |
| 2011/0213218 A1* | 9/2011 | Weiner | A61B 5/0002 600/301 |
| 2013/0158364 A1* | 6/2013 | Hayn | A61B 5/1116 600/301 |

\* cited by examiner

DEVICE FOR MONITORING FOR EFFECTIVENESS OF HEART FAILURE THERAPY

RELATED APPLICATIONS

The present application is related to and claims priority to U.S. Provisional Patent Application Ser. No. 62/025,683, filed on Jul. 17, 2014. The subject matter disclosed in that provisional application is hereby expressly incorporated into the present application in its entirety.

FIELD

Disclosed embodiments pertain to the field of electronic monitoring of biometrics. More particularly, disclosed embodiments are in the field of measuring and monitoring the metrics commonly associated with Heart Failure (HF), also commonly referred to as Congestive Heart Failure (CHF).

BACKGROUND

HF is a condition in which the heart does not sufficiently pump blood to and from the organs of the body. The American Heart Association estimates that there are approximately six million Americans living with CHF, and there are approximately 53,000 deaths due to CHF each year, making it one of the most significant public health burdens in the United States. As blood is pumped progressively less effectively due to CHF, fluid can aggregate in the legs, a condition called peripheral edema, and in the lungs, a condition called pulmonary edema. Pulmonary edema can cause significant difficulty to breathing, and reduce the effectiveness of breathing in saturating the blood with oxygen. Other symptoms of HF can include cardiac arrhythmias, hypertrophy of the heart muscle, and significant fluid retention and weight gain and subsequent hypertension, also known as high blood pressure. To treat HF, patients may be started on daily regimens of drugs such as antiarrhythmics, antihypertensives, anticoagulants, and diuretics. Diuretics cause an increase in excretion, via urination, of fluid and can thus contribute to reducing the fluid retention that causes hypertension, pulmonary edema, peripheral edema, and low blood oxygen saturation.

The current state of daily monitoring in the home for the effectiveness of treatments is currently limited. The most common methods of monitoring consist of the patient stepping on a bathroom scale every morning to measure his or her body weight. If the patient's weight is significantly higher (approximately 3 pounds higher) than it was on the previous day, it is concluded that the patient is retaining extra fluid and that the dose of diuretic needs to be changed. This method is limited insofar as it only measures one metric. Further, because there are numerous other causes for weight gain, including constipation and consumption of large quantities of food, this method is considered crude and not particularly sensitive. This method of monitoring also provides information only regarding the effectiveness of diuretic therapy and not of other therapies that the patient may be using, and may need to be monitored. It is desirable to provide an at home device that is as user friendly and familiar as a bathroom scale, but provides other significant heart-failure related biometric data. One significant example is monitoring ECG to determine effectiveness of antiarrhythmics. Another example is monitoring the patient's risk of falling, which could pose significant life danger if the patient has taken anticoagulant medication.

As an alternative method to daily weight monitoring, some patients measure blood pressure on a daily basis and report the results. There exists no device that performs a comprehensive analysis of numerous HF-related biometrics in the patient's home and transmits all results instantaneously to the patient's healthcare provider.

SUMMARY

The above problems, as well as other problems which include patient compliance, may be addressed by various aspects of an inventive device for monitoring for effectiveness of heart failure therapy. Disclosed embodiments of such a device enable an electronic method of measuring the biometrics that may be the most indicative of the state of HF in a patient.

In accordance with at least one disclosed embodiment, the device measures weight, respiratory rate, pulmonary and pedal impedance as indicators of edema, 6 standard electrocardiography (ECG) leads, pulse wave transit time, and pulse oximetry.

In accordance with at least one disclosed embodiment, the device also calculates the patient's ability to balance. The device may be designed as a bathroom scale with a vertical bar rising from the top of the scale, and with handlebars at the top of the vertical bar. The patient is to stand on the scale and grip the handlebars. The handlebars may be made of a conductive material and thus serve as electrodes. The handlebar electrodes and the electrodes on the scale, which make contact with the hands and feet, acquire the respiratory rate, biompedance of the lungs and the feet as correlates of levels of pulmonary and pedal edema, respectively, and ECG. Load bearing sensors in the scale measure the weight. Near one of the handlebars, a finger clip containing light LEDs and sensors, acquires pulse oximetry from the patient. Analyzing simultaneous signals from both the pulse oximetry signal and ECG—particularly comparing the times of R wave occurrence on ECG, and pulse arrival in the finger on pulse oximetry—yields Pulse Wave Transit Time, a correlate of systolic blood pressure.

Each of the metrics may be transmitted either via hard-wired connection or via Bluetooth to a Tablet computer, which then transmits the data via a cellular signal to a remote server that may be accessible remotely by the patient's healthcare provider. Each of the biometrics can easily be measured by the disclosed compact device without the assistance of a caregiver or healthcare provider, and without extensive medical knowledge or training for the patient or user. Each of the biometrics can be measured when the patient steps on the scale, automatically, without patient having to remember to take a plurality of different measurements or select a particular measurement program. Additional features of the present disclosure will become apparent to those skilled in the art upon consideration of illustrative embodiments exemplifying the best mode of carrying out the disclosure as presently perceived.

DETAILED DESCRIPTION

Disclosed embodiments address conventional problems with heart failure therapy by enabling electronic measuring of biometrics most indicative of the state of HF in a patient. This is performed, for example, by providing a single device that measures weight, respiratory rate, pulmonary and pedal impedance as indicators of edema, 6 standard electrocardiography (ECG) leads, pulse wave transit time, and pulse oximetry.

Figure 1:
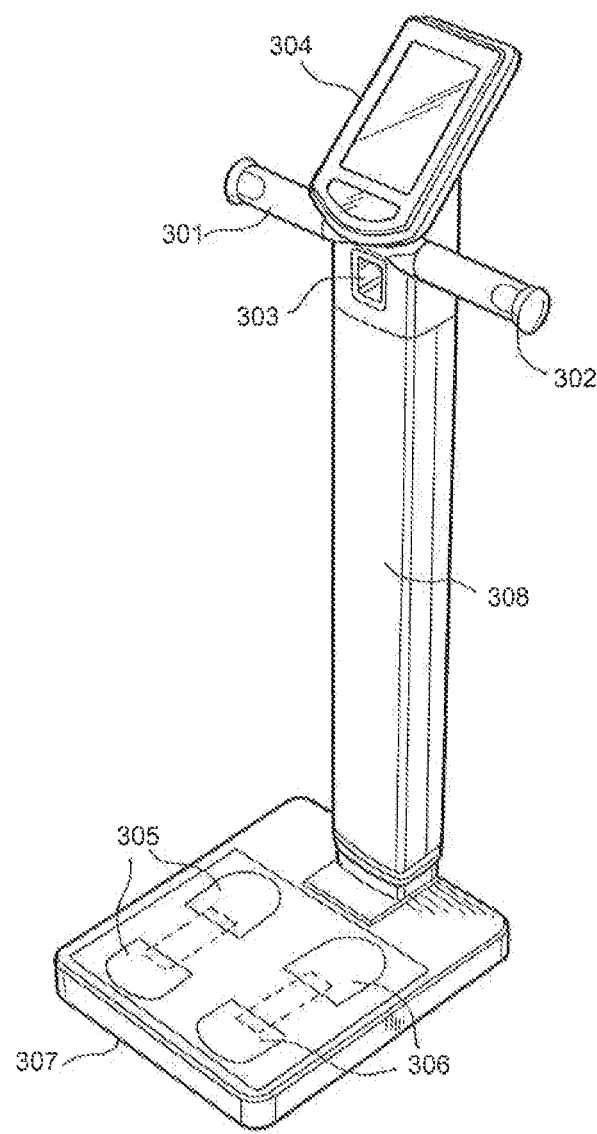
FIG. 1 is an isometric view of a device in accordance with the disclosed embodiments of the invention.

As illustrated in FIG. 1, the device may comprise a weight scale 100, with at least one load cell sensor (which interacts with the processor 120 as illustrated and explained in more detail with relation to FIG. 2 below) to measure weight on the left and right sides of the scale. A vertical bar rises from the base of the scale and two metallic handlebars 301, 302 and a pulse oximeter finger clip 303. Handlebars 301, 302 extend from the bottom of the weight scale 100 to an adjustable height. The handlebars 301, 302 have two metallic electrodes located on the left and right side, each. Handlebar electrodes depicted are round, but may also be of a different shape. A specialized finger clip 303 acting containing a pulse oximeter may be attached to the right handlebar 302 electrode with a wire. In another embodiment of the invention, the pulse oximeter may be embedded into the handlebar 301, 302, so that the handlebar and light sensor may be one piece.

In accordance with at least one embodiment, the device 100 may include a hinge between the stalk 308 and the bottom base 307, allowing folding of the device 100 for easy storage and shipping. Fitting within a standard sized shipping box, as opposed to a premium-priced oversized box may be useful for the device to be able to be distributed to the population in mass. Any hinge mechanism may be used, as long as it may support the weight of the stalk and bottom base. Many commercial off the shelf hinges are good candidates for this function, e.g. hinges of doors, scooters, carriages, etc.

In use, a patient steps onto the scale device 100 with bare feet, with each foot touching an electrode 305, 306, and also grips the top handlebar 301, 302 with each hand. Additionally, the patient may clip on a light sensor finger clip or tube 303 on the right hand. The processor 120 senses the patient's weight on the scale 307 and automatically powers on.

The electronics processor 120 turns on the LCD screen 304 of the user interface 190 and displays a prompt to the user, via a visual indication on the screen and/or audio alert via audio speaker 115, instructing the patient to clip on the finger clip 303 to his/her finger. Once the device 100 detects that the user has put on the finger clip 303 and held the handlebars (handlebar electrodes 301, 302), the processor 120 controls the other components illustrated in FIG. 22 to acquire biometric data about the user over a specified period of time. The processor 120 then controls the LCD screen 304 to display a message to the user while it is acquiring biometric data.

The processor 120 determines if the user is holding onto the handlebars/hand electrodes 301, 302 utilizing a lead off detect feature built into conventionally available, off-the-shelf, analog frontend Integrated Circuits (ICs). This lead off detect feature works by sending a low amperage signal into one electrode and checking to see if the signal is present on a different electrode. If the signal is present, a relatively low resistance electrical path exists between both electrodes, indicating that the user is holding both electrodes. The path between electrodes is the user's skin and body. If the signal is not present, there exists no low resistance path and the user is not holding both electrodes.

In accordance with at least one embodiment of the invention, the processor 120 may use lead off detection on all leads of the device, including the handlebars and footpads. If a lead-off event is detected, the processor 120 displays an error message and/or a corrective instruction on the screen, e.g. "Please hold the handlebars." The device may also play an audio message relating to the corrective instruction to aid the visually impaired.

Figure 2:
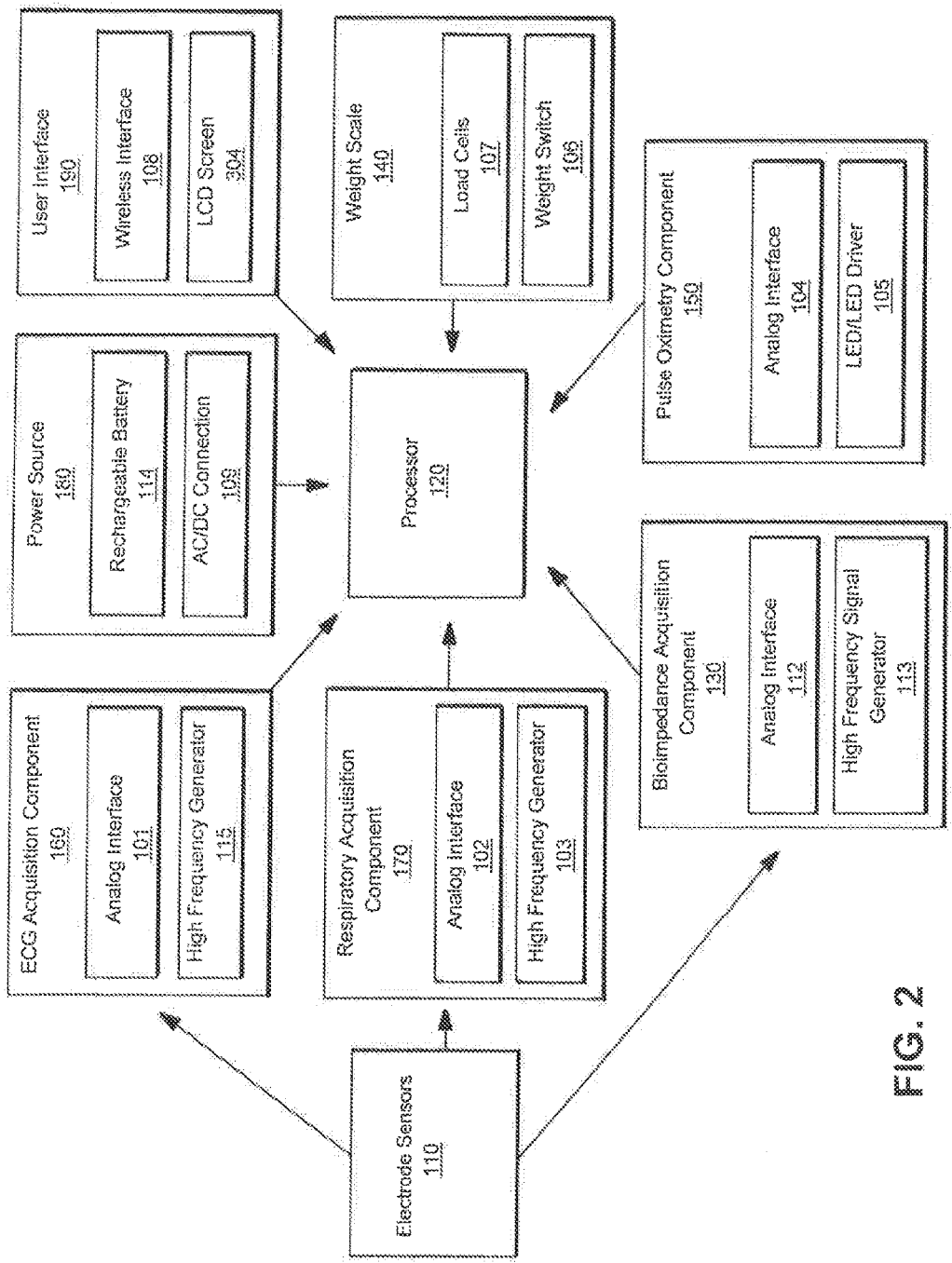
FIG. 2 is a diagram of the signal acquisition and transmission hardware.

As illustrated in FIG. 2, various components interact with one another to gather data for determining the biometrics most indicative of HF of a patient. Therefore, as shown in FIG. 2, the device 100 includes a plurality of electrode sensors 110, processor 120, a bioimpedance acquisition component 130, a weight scale 140, pulse oximetry component 150, EKG acquisition component 160, respiratory acquisition component 170, a power source 180, and a user interface 190.

The plurality of electrode sensors 110 are positioned and coupled to other components of the device 100 to gather biometric data about a patient. Each electrode sensor may be implemented as a lead with a sensor interacting with the patient and being coupled to the other components of the device 100.

Further, because skin conductance is an indicator of physiological stress in a patient, in accordance with at least one embodiment, each handlebar electrode may be split into two separate electrically conductive surfaces. Skin conductance may be determined by measuring the resistance between the two conductive surfaces in each handlebar electrode 301, 302. An increase in skin conductance, caused by an increase in perspiration, results in a decrease in ohms resistance. The resistance may be measured via an analog to digital conversion performed by the processor 120 or another suitable component within the device 100.

The bioimpedance acquisition component 130 includes an analog interface 112 and a high frequency signal generator/receiver 113. In accordance with at least one embodiment, the device may be configured to enable determination of another useful metric, which is the quantification of edema in the patient's legs. An increase in water content in a patient, i.e. an increase in swelling is evidenced by a decrease bioimpedance. The mathematical relationships between impedance and patient water volume have been published and rely on patient information such as age, weight, and body type.

Thus, in accordance with at least one embodiment, the processor 120 may acquire the user's bioimpedance via a dedicated bioimpedance component 130. The bioimpedance component 130 may include an analog interface 112 that may apply a high frequency voltage signal across the user's legs, e.g., from the left footpad electrode sensor 305 to the right footpad electrode sensor 306, and perform an analog to digital conversion of the voltage between the two electrodes over a sampling period. The high frequency signals may subsequently be fed through a bandpass filter to prevent noise errors. Thus, the device 100 can calculate a peripheral edema measurement with electrodes in the weight scale measuring bioimpedance across the legs.

Likewise, the device 100 can calculate a pulmonary edema measurement by measuring bioimpedance across the arms. The edema measurements provide a direct correlation to volume of fluid retained. Therefore, such measurements can be used to provide a fluid volume measure. The device's processor 120 (or a remote server) may be configured to compare a change in fluid volume to a change in weight, by comparing current values to stored previous values, to distinguish if the change in weight is due to fluid retention rather than some other cause.

For example, if a patient gained 1 kg of weight and an increase in fluid volume of 1 liter is detected, then the system will indicate the weight gain is due to fluid retention. Alternatively, if the patient has gained 1 kg in weight and a corresponding gain of 1 liter of fluid is not detected, the system will be able to identify and indicate that the weight gain is not due to fluid retention.

The system may also compare relative fluctuations in volume and weight to determine if the patient weight gain is due to fluid retention. For example, if the device 100 determines the patient's weight has increased and his bioimpedance levels have decreased, the system can indicate that the weight gain is at least partially due to fluid retention. Alternatively, if the device 100 detects a weight increase in the patient and a decrease in bioimpedance, the device 100 can indicate that the weight gain is due to factors other than fluid retention.

The weight scale 140 includes a plurality of load cell sensors 107, e.g., 2 or four load cell sensors) and a weight switch 106. An analog voltage output from the load cell sensors 107 may be linearly related to, and indicative of, the patient's weight. The empty weight of the scale may be subtracted from all readings.

The patient's ability to balance may be quantified by comparing the load cell measurements of the left and right side of the scale 140 over time. A constant distribution of weight on the left and right sides of the scale 140 indicates a strong ability to balance and a low risk of falling. The processor 120 performs an analog to digital conversion on the output of the left side and right side load cells over a sampling period. If the distribution of the weight on the two sides varies significantly over time or in amplitude, this can indicate that the patient has difficulty balancing and may be at a high risk for falling. Specifically, the balance measurement may be calculated by computing the power spectral density and variance of the two signals obtained from the left and right sides of the scale 140. In another embodiment, additional individual load cell measurements may be used to acquire a more precise balance measurement.

While in sleep state, the processor 120 continuously measures the weight on the load cells 107. This force may be quantified by performing an analog to digital conversion on the excitation voltage of the output of the load cells 107. While the force measured on the load cells 107 may be below a preloaded threshold, i.e. the weight on the scale 140 may be below a specific weight, the device 100 may remain in sleep mode. Once the force on the load cells 107 rises above the preloaded threshold, i.e. the weight on the scale is above a specific weight because someone or something is positioned on it, the device 100 exits sleep mode and powers up.

In the case of a footpad lead-off event, in the absence of a handlebar lead-off event, i.e., the user/patient is holding the handlebars but has shoes on or is not stepping on both footpads, the processor 120 may control the LED screen 304 to display a corrective instruction, e.g., "Please Take Off Your Shoes".

If at any point in the process, excluding while the device 100 is in sleep mode or uploading data, the processor 120 detects that the weight on the scale is below a specified threshold, i.e. the user prematurely stepped off the scale 140, the processor 120 may control the LCD screen 304 to display an error message or to control the audio speaker 115 to play an audio message to alert the user/patient.

The pulse oximetry component 150 includes an analog interface 104 and an LED/LED driver 105 which are both included in the finger clip 303 illustrated in FIG. 1. The processor 120 determines when the user puts on the finger clip 303 by performing an analog to digital conversion on the output signal of the pulse oximeter finger clip 303. If the measured value indicates a high light level above a pre-specified threshold, i.e. the light from the LED/LED driver 105 in the finger clip 303 is hitting a light sensor included in the analog interface 104 directly, the processor 120 determines that the user has not placed his finger in the clip 303. On the other hand, if the measured value detected by the light sensor indicates a low light level below a pre-specified threshold, i.e. the light from the LED/LED driver 105 in the clip 303 is being obstructed by a finger or object, the processor 120 determines that the user has placed his finger in the clip 303.

The functionality of the pulse oximeter sensor finger clip 303 may be implemented as such or implemented using a pulse oximeter embedded in the handlebar 301, 302. In such a handlebar implementation, the pulse oximeter sensor may comprise a red LED and infrared LED coupled with a light sensor. In the case of the finger clip 303, the red and infrared LED/LED drivers 105 may alternate shining through the patient's finger, while a light sensor 104 on the opposite side of the finger measures light absorption through the finger.

The resulting signal of the light sensor 104 may be a photoplethysmogram (PPG), which can be processed to yield blood oxygen saturation percentages as well as heart rate. Blood oxygen saturation may be determined by calculating the ratio of the light absorbance of the red and Infrared led at the diastole and systole and scaling by a constant factor. The finger clip 303 may be attached by wiring to—and when not in use rests in—a housing socket in the top center of the stalk of the device 100. All other electronics may be securely mounted, and hidden, inside the base 307 of the device 100.

The processor 120 can use the measured pulse oximetry from the pulse oximetry component 150 and bioimpedance from the bioimpedance component 130 described above to determine if a change in patient pulse oximetry is a result of fluid retention in the lungs based on the signals received from the hand electrodes and a photoplethysmogram (PPG) generated by the pulse oximeter. For example, if pulse oximetry is reduced, a corresponding reduction in measured bioimpedance across the hand electrodes would result in a processor determination that fluid filling the lungs is preventing the lungs from oxygenating the blood. The signals received from the hand electrodes may include bioimpedance detected across the hand electrodes and bioimpedance detected across the foot electrodes. The measured bioimpedance may include the bioimpedance across the chest of a user.

The ECG acquisition component 160 includes an analog interface 101 and utilizes data gathered by all or some subset of the electrode sensors 110. The processor 120 acquires an ECG signal by performing an analog to digital conversion of the voltage potentials across all electrodes, across the patient's arms and legs. This may be performed using the analog interface 101. Thus, it should be understood that the processor 120 may communicate via the analog interface 101 over a digital serial connection.

For the purpose of determining ECG data, all ECG leads utilized may be standard leads. Thus, for example, Lead I may be the voltage between the left handlebar electrode 301 to the right handlebar electrode 302. LEAD II may be the voltage between the left scale electrode 305 and the right handlebar electrode 302. Lead III may be the voltage between the left scale electrode 305 and the left handlebar electrode 301. In this example, the right scale electrode may serve as the right leg drive. The vector of Lead I plus the vector of Lead III equals the vector or Lead II. That is, Lead I+Lead III=Lead II. Thus, any one of these leads can be derived from the other two leads. Therefore, derivation of an ECG (including aVF, aVL, and aVR) may be performed using the processor 120 or be performed remotely. Accordingly, in at least one embodiment, the ECG data may be transmitted to a remote server for further processing (as explained in relation to FIG. 3 below)

Further, data from individual components of the device 100 may be combined to determine additional biometric data. For example, systolic blood pressure may be determined via Pulse Wave Velocity calculation, by analyzing the difference between the ECG R wave peak, as determined by the ECG acquisition component 160, and the peak of the PPG signal of the pulse oximeter component 150). The difference in time between the ECG R wave and PPG peak represents the time it takes for blood to pump from the heart to the user's fingertip, which correlates to systolic blood pressure. As above, this analysis may be performed using the processor 120 or be performed remotely at a server (as discussed in relation to FIG. 3 below).

The respiratory acquisition component 170 includes equipment used to gather respiratory data for a user/patient. Thus, the processor 120 may acquire patient respiratory rate data by applying a high frequency voltage signal across the patient's arms, e.g., from the left electrode 301 to the right electrode 302. Subsequently, the analog front end 102 performs an analog to digital conversion of the voltage between the two electrodes over time. As a patient respires, the patient's thorax expands and contracts in correlation to breathing, causing a change in impedance over time, thereby affecting voltage. In accordance with at least one embodiment, a high frequency signal may be generated by a high frequency signal generator 103, applied to the user/patient and subsequently bandpass filtered to prevent noise errors. It should be understood that in some embodiments the plurality of high frequency generators disclosed may be a single high frequency generator for ECG, Respiratory acquisition, and bioimpedance acquisition components.

In accordance with at least one embodiment, both the ECG and respiratory signals may be sampled over a period of time and stored into memory (not illustrated but resident in the processor 120 or coupled to it) or transmitted immediately wirelessly to a remote server).

The power source 180 may be AC to DC wall converter 109 to power the device 100. In another embodiment of the invention, the device contains a rechargeable battery 114 that the patient may recharge. Similarly, in another embodiment, the device may be powered by alkaline batteries that the patient may replace.

The user interface 190 May be a tablet computer and with LCD touch screen 304 embedded in the top handlebar 301,302 sections. The user interface 190 acts as the primary user interface, displaying information visually on its LCD screen 304 and also alerting users with sound with the tablet's built-in speakers 115. The screen 304 displays content to the patient. The screen 304 may indicate to the patient how many seconds remain in a recording of data process or may display current values from that day's use. The screen 304 may also display the user weight and current measurement of heart rate. The screen 304 may also display other content, including but not limited to previous sensor values, target values for healthy lifestyle, and messages from health care personnel. The screen 304 may be controlled by a processor (not shown) standard to a tablet computer and embedded in the device. In another embodiment, a Smartphone 202 (as seen below with respect to FIG. 3) may be used in addition to, or instead of, the built-in tablet computer screen 304. The processor 120 communicates with the Smartphone 202 via a wired connection or via a wireless interface 108, such as WiFi or Bluetooth.

After the device has completed acquiring the user's biometric data over a period of time, the device may display a Symptoms Survey on the built-in LCD screen 303. The user interacts with the survey and selects/inputs information via the touch-screen interface built-into the tablet's LCD screen 303. For example, the survey display may consist of three different icons representing different mood levels. The end user selects the icon that most closely represents his current mood by tapping the icon on the touch screen LCD display with his finger.

After acquiring all of the biometric data for a period of time, as well as the user's survey information the processor in the user interface 190 uploads all of the biometric data to a remote server via the user interface's wireless interface 108 connected to the Internet, e.g. WiFi, cellular. The processor sends a signal to the user interface which notifies the user that he may step off the scale. After the user steps off, the device 100 may return to its initial sleep mode state, conserving power.

Figure 3:
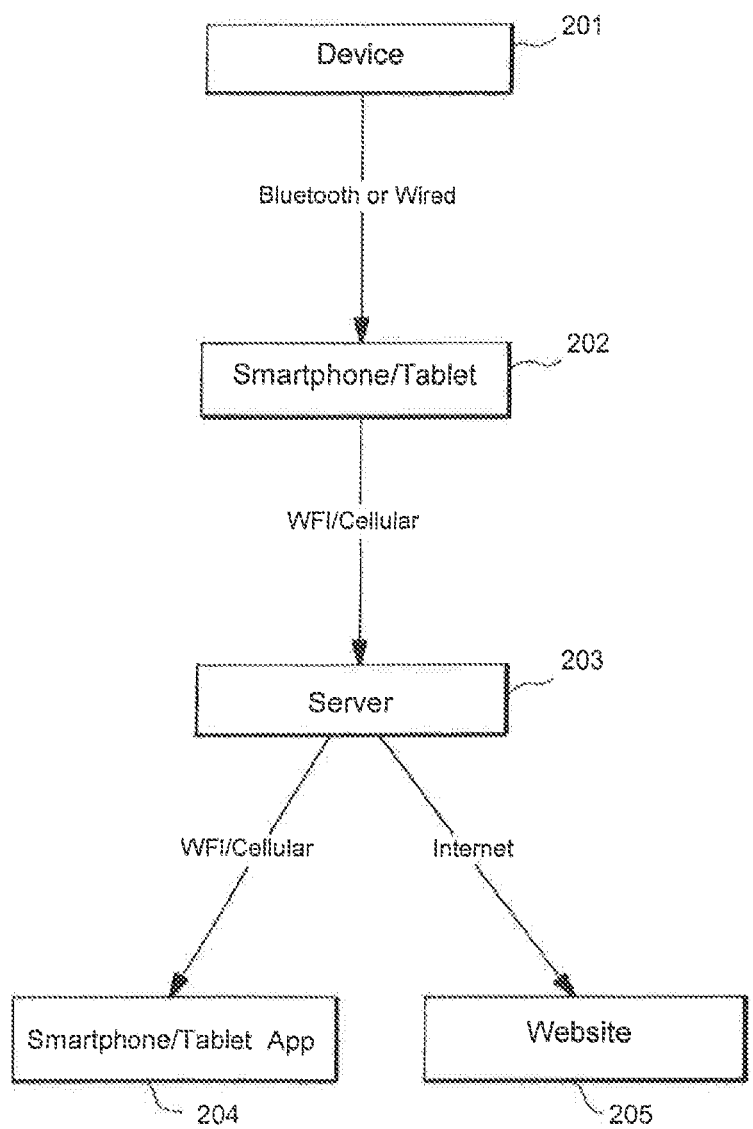
FIG. 3 is a diagram of the flow of signal data from the device to an app or website.

As seen in FIG. 3, the device 100 is in communication with the user interface 190, which may further be in communication with a server 203. Server 203 may further process and store data as described above and further with respect to FIG. 4 below. Server 203 may then communicate the biometric data and trends to a user interface 204 which may be the same user interface in communications with the device 100, or may be one or more additional user interfaces accessible by a care provider and/or patient. Server 203 may alternatively or additionally communicate the biometric data and trends to a website 205.

As stated above, the processor 120 has a direct communication link and control to the user interface 190 via a wired USB connection. The processor 120 sends all the biometric data in a digital serial format over the USB interface to the tablet. The user interface 190 receives the digital serial data, compresses the data, and then uploads via HTTP to a remote server dedicated to receiving biometric data. The server 203 receives the data and then stores it into a database or other storage medium.

Device 100 may record the ECG, Respiratory, Weight, and PPG signals over a period of time (for example, over sixty seconds) and then transmit the signals wirelessly, using WiFi or cellular 108, to a computer server 203 for further processing and storage. The device 100 may also store the data onboard for later access via USB, memory card, or wireless. The device 100 may also transmit the data to a Smartphone/tablet which would relay the data to a remote server 203.

The remote server 203 stores and analyzes the data from each patient. For example, the remote server 203 may determine any of the biometrics previously disclosed including user balance. Trends of patient's biometric data may be calculated and determined over time and stored on the remote server 203.

Figure 4:
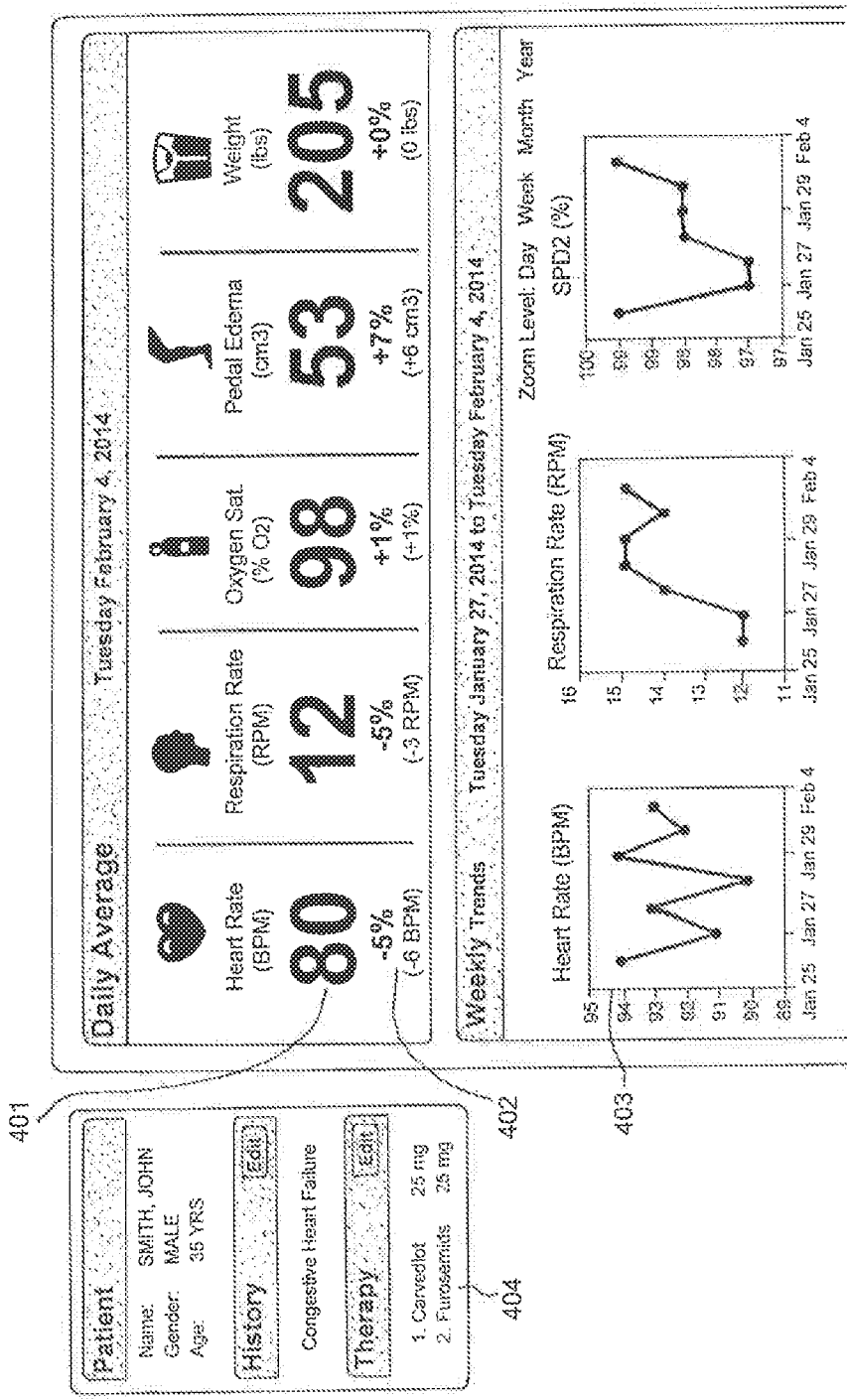
FIG. 4 is a view of the website or app relating to this device.
Figure 5:
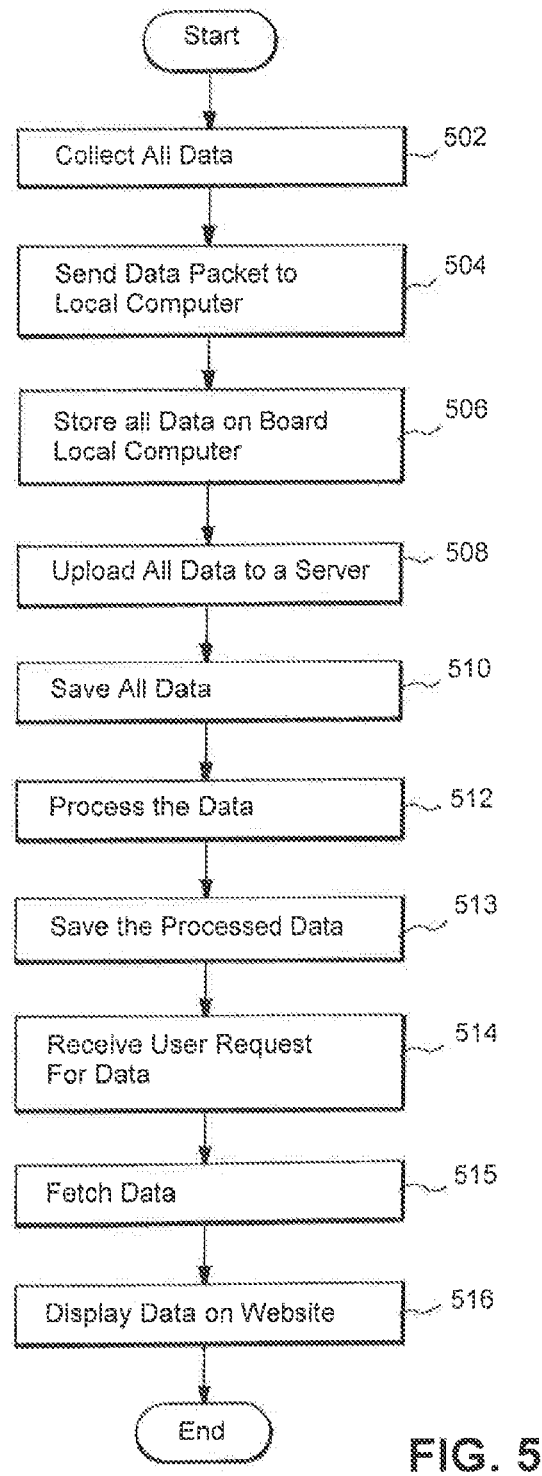
FIG. 5 is one embodiment of movement of data from the measurement device to other devices in the system.

In some embodiments, an online website 205 provides an interface for health care personnel and/or patients to view their signals 401,402 from a previous point in time. FIG. 4 provides an exemplary embodiment of such a website or smartphone/tablet app. Additionally, the website 205 may provide graphical output 403 representing patient's signals over time. Furthermore, the website 205 may offer functionality 404 for health care personnel to send messages, such as updated drug therapies, to patients via their interface LCD screens 304 or Smartphone/tablet 202 apps. Health care personnel may also set alert conditions for them to receive text message or email alerts if patients exceed specific alert conditions. The website 205 offers health care personnel the ability to track their patient's health over time and monitor the effectiveness of treatment.

The online website, or in one embodiment onboard the Smartphone/tablet app, displays the most recent values 401 calculated for patients. Furthermore, percentage change 402 and amount of change 402 may be displayed to provide health care personnel, and color-coded representing "safe" value ranges for each patient. Additionally, patient's health values may be plotted over time to graphically display trends 403

In a method of operation, biometric data are simultaneously collected from a user over a period of time 502. A biometric data packet is sent from the measurement device via a wireless protocol or wired connection to a local processing device 504 where it is stored 506. The local processing device may then upload the stored data, along with additional user inputs to a remote server via a POST request 508. The remote server receives the post request and saves the raw data received from the local processing device 510. The remote server may then process the data by filtering it, and or calculating physiological values and trends for the user 512. The processed data may then be requested 514 from the post server via a POST request, fetched from storage and displayed to the user using a JSON reply 516. For example, the fetched data may be requested by and displayed on a website or web smartphone/tablet app.

Disclosed embodiments solve a technical problem in the conventional art in that there is no conventional device that is able to measure biometric data associated with heart failure in a user friendly manner and able to provide multifactor biometric data, including, for example, ECG (to determine effectiveness of antiarrhythmics), monitoring a patient's risk of falling (which could pose significant life danger if the patient has taken anticoagulant medication), respiration, edema, heart rate, pulse oximetry, etc.

Each of the metrics may be measured in an automated fashion with little or nothing more to trigger the measuring than a user stepping onto the scale and holding the handbar/electrode assembly. Subsequently, the data gathered via the device may be transmitted either via hardwired connection or via Bluetooth to a Tablet computer, which may then transmit that data via a cellular signal to a remote server that may be accessible remotely by the patient's healthcare provider. Each of the biometrics can easily be measured by the disclosed compact device without the assistance of a caregiver or healthcare provider, and without extensive medical knowledge or training for the patient or user. Each of the biometrics can be measured when the patient steps on the scale, automatically, without patient having to remember to take a plurality of different measurements or select a particular measurement program.

Thus, it should be understood that the disclosed invention contemplates a controller for a weight scale system that may include a processor; and a memory having stored therein a plurality of instructions that when executed by the processor cause the controller to switch the weight scale system from a sleep mode to an active mode upon detection of at least a predetermined weight on the weight scale, detect that a user's hands and feet are in contact with predetermined areas of the scale system, acquire biometric data from the weight scale system for a predetermined period of time in response to the detection, and transmit the acquired biometric data to a user interface comprising a display tablet for transmission to a remote server. The processor may be further configured to detect if the user's hands and/or feet lose contact with predetermined areas of the scale system during the predetermined period of time and display instructions to the user to regain contact with the predetermined areas. The processor may be further configured to discard the previously acquired biometric data and acquire a new set of biometric data for the predetermined period of time in response to detection that the user's hand and feet have regained contact with the predetermined areas. The processor may be further configured to stop acquiring biometric data after a predetermined period of time has passed and notify a user that the acquisition is complete.

A system may be provided for measuring biometrics associated with congestive heart failure and may include a weight scale including foot electrodes and a support extending from the weight scale, the support having handlebars with electrodes for measuring biometrics, a user interface for displaying user history, target biometric values, and messages to a user; and means for starting measurement of a plurality of biometrics, receiving biometric data over a predetermined period of time, and processing the biometric data, wherein said means may comprise a controller as described above. The biometric data may include ECG, respiratory, bioimpedance, and weight data. The messages may include an alert that the user has stepped off the scale too early and a prompt to step back on the scale. The messages may include an interactive symptoms survey prompting the user to select one or more symptoms on the display. The user interface may transmit the one or more selected symptoms along with the biometric data to a remote server. The user interface may be integrated or wirelessly connected to the weight scale. The system may include electrodes, the electrodes may be two separate electrically conductive surfaces on a left handlebar and two separate electrically conductive surfaces on the right handlebar. The system may include a fingerclip mounted on the support that measures pulse oximetry and the messages include a prompt to use the fingerclip mounted to the support. The means for starting a measurement may comprise a processor configured to continuously scan load cells in the weight scale and exits a sleep state when a predetermined weight threshold is detected on the weight scale.

The user interface of the system may transmit the biometric data to a remote server. The remote server may include a memory to store the received signals and be further configured to calculate heart rate, respiration rate, and SPO2 based on the received biometric data. The remote server may be further configured to measure balance and water content based on the received biometric data.

A weight measuring device may be contemplated including a system as disclosed above, with the weight scale including load cell sensors; a plurality of hand and foot electrodes mounted to the scale; and a processor may be configured to determine whether a change in patient weight is a result of fluid retention based on signals received from the hand and foot electrodes and a weight signal generated by the load cell sensors and to notify a user of the determination. The processor may be on board the scale or may be comprised in a remote server.

The remote server may receive biometric data, analyze the biometric data, and determine trends in the data over time. The remote server may provide and update biometric data to a user and a physician, in particular to update a history of analyzed data for the patient and transmit the data to a website accessible by the user and a physician. The remote server may distinguish weight gain due to fluid retention from weight gain due to other causes based on the collected biometric data. The remote server may analyze the data and provide patient-specific feedback to the user on the user interface based on the analyzed data. The patient-specific feedback may include whether the analyzed data falls inside pre-determined safe ranges for the user.

The weight measuring device may further include a signal generator, wherein the signals received from the hand and foot electrodes are bioimpedance signals. The processor may determine the change in weight is due to fluid retention when increase in weight is detected for the user and an overall decrease in bioimpedance. The signals received from the hand and foot electrodes may include a bioimpedance detected across the hand electrodes and a bioimpedance detected across the foot electrodes. The processor may calculate a water retention volume based on the bioimpedance detected across the hand electrodes and the feet electrodes.

Although certain embodiments have been described and illustrated in exemplary forms with a certain degree of particularity, it is noted that the description and illustrations have been made by way of example only. Numerous changes in the details of construction, combination, and arrangement of parts and operations may be made. Accordingly, such changes are intended to be included within the scope of the disclosure, the protected scope of which is defined by the claims.

The invention claimed is:

1. A system for measuring biometrics associated with congestive heart failure, the system comprising:
   a weight scale including foot electrodes and a support extending from the weight scale, the support having handlebars with electrodes for measuring biometrics,
   a user interface for displaying user history, target biometric values, and messages to a user;
   means for simultaneously starting measurement of a plurality of biometrics, receiving biometric data over a predetermined period of time, and processing the biometric data, and
   a remote server, including memory, configured to receive and store the biometric data from the means for simultaneously starting measurement and calculate heart rate, respiration rate, SpO2, and blood pressure based on the biometric data,
   wherein the messages include an alert that the user has stepped off the scale too early in response to the means sensing the weight below a specific threshold and a prompt to step back on the scale,
   wherein the means for simultaneously starting measurement comprises a processor configured to continuously scan load cells in the weight scale, detect contact of hands and feet of the user with predetermined areas of the scale system, and exit a sleep state when a predetermined weight threshold is detected on the weight scale.

2. The system of claim 1, wherein the biometric data include ECG, respiratory, bioimpedance, and weight data.

3. The system of claim 1, wherein the system includes a fingerclip mounted on the support that measures pulse oximetry and the messages include a prompt to use the fingerclip mounted to the support.

4. The system of claim 1, wherein the messages include an interactive symptoms survey prompting the user to select one or more symptoms on the display.

5. The system according to claim 4, wherein the user interface transmits the one or more selected symptoms along with the biometric data to the remote server.

6. The system of claim 5, wherein the remote server is configured to update a history of analyzed data for the patient and transmit the data to a website accessible by the user and a physician.

7. The system of claim 1, wherein the user interface is a display tablet integrated or wirelessly connected to the weight scale.

8. The system of claim 1, wherein the electrodes comprise two separate electrically conductive surfaces on a left handlebar and two separate electrically conductive surfaces on the right handlebar and the means is configured to measure skin conductance through the conductive surfaces on at least one of the handlebars and determine stress.

9. The system of claim 1, wherein the remote server is configured to receive the biometric data, analyze the biometric data, and determine trends in the biometric data over time.

10. The system of claim 1, wherein the remote server is configured to provide and update biometric data to a user and a physician.

11. The system of claim 1, wherein the remote server is configured to analyze the biometric data and provide patient-specific feedback to the user on the user interface based on the analyzed data.

12. The system of claim 11, wherein the patient-specific feedback includes whether the analyzed data falls inside pre-determined safe ranges for the user.

13. The system of claim 1, wherein the user interface transmits the biometric data to the remote server.

14. The system of claim 13, wherein the remote server is configured to calculate a peripheral edema value using bioimpedance data collected from the foot electrodes.

15. The system of claim 13, wherein the remote server is configured to calculate a pulmonary edema value using bioimpedance data collected from the electrodes on the handlebars.

16. The system of claim 13, wherein the remote server is configured to distinguish weight gain due to fluid retention from weight gain due to other causes based on the collected biometric data.

17. The system of claim 1, wherein the remote server is further configured to measure balance and water content based on the received biometric data.

18. A controller for a weight scale system comprising:
   a processor; and
   a memory having stored therein a plurality of instructions that when executed by the processor cause the controller to:
      switch the weight scale system from a sleep mode to an active mode upon detection of at least a predetermined weight on the weight scale;
      detect that a user's hands and feet are in contact with predetermined areas of the scale system;
      acquire biometric data from the weight scale system for a predetermined period of time in response to the detection; and transmit the acquired biometric data to the display tablet for transmission to a remote server, wherein the processor is further configured to detect the user's hands and feet losing contact with predetermined areas of the scale system during the predetermined period of time and display instructions to the user to regain contact with the predetermined areas, wherein the processor is configured to sense a weight below a specific threshold and display an alert and a prompt to step back on the scale, wherein the processor is further configured to determine whether a change in a patient pulse oximetry signal is a result of fluid retention in the lungs based on the acquired biometric data, and notify a user of the determination.

19. The controller of claim 18, wherein the processor is further configured to discard previously acquired biometric data and acquire a new set of biometric data for the predetermined period of time in response to detection that the user's hand and feet have regained contact with the predetermined areas.

20. The controller of claim 18, wherein the processor is further configured to stop acquiring biometric data after a predetermined period of time has passed and notify a user that the acquisition is complete.

21. A weight measuring device comprising:
  a scale including load cell sensors;
  a plurality of hand and foot electrodes mounted to the scale, the hand electrodes mounted to a stalk that is coupled to a base of the device via a hinge mechanism for folding of the device; and
  a controller comprising:
    a processor; and
    a memory having stored therein a plurality of instructions that when executed by the processor cause the controller to:
      switch the weight scale system from a sleep mode to an active mode upon detection of at least a predetermined weight on the weight scale;
      detect that a user's hands and feet are in contact with predetermined areas of the scale system;
      acquire biometric data from the weight scale system for a predetermined period of time in response to the detection; and
      transmit the acquired biometric data to a display tablet for transmission to a remote server,
    wherein the processor is further configured to detect the user's hands and feet losing contact with predetermined areas of the scale system during the predetermined period of time and display instructions to the user to regain contact with the predetermined areas,
    wherein the processor is configured to sense a weight below a specific threshold and display an alert and a prompt to step back on the scale,
    wherein the processor is further configured to determine whether a change in a patient pulse oximetry signal is a result of fluid retention in the lungs based on the acquired biometric data and notify a user of the determination.

22. The weight measuring device of claim 21, wherein biometric data received from the hand and foot electrodes comprises bioimpedance data.

23. The weight measuring device of claim 21, wherein biometric data received from the hand and foot electrodes includes a bioimpedance detected across the hand electrodes and a bioimpedance detected across the foot electrodes.

24. The weight measurement device of claim 23, wherein the processor is configured to calculate a water retention volume based on the bioimpedance detected across the hand electrodes and the foot electrodes.

* * * * *